United States Patent [19]

Schoeller et al.

[11] Patent Number: 4,719,351

[45] Date of Patent: Jan. 12, 1988

[54] PROCESS FOR DETERMINING OXIDATION-DEPENDENT CHARACTERISTICS OF SIMILAR PLASTIC ARTICLES, AS WELL AS USES OF THE PROCESS AND APPARATUS FOR PERFORMING THE PROCESS ON LARGE INJECTION MOULDED PRODUCTS, PARTICULARLY BOTTLE CRATES

[75] Inventors: Christoph Schoeller; Martin Schoeller, both of Zuoz, Switzerland

[73] Assignee: Alexander Schoeller & Co. AG, Romont, Switzerland

[21] Appl. No.: 822,404

[22] PCT Filed: May 1, 1985

[86] PCT No.: PCT/CH85/00068

§ 371 Date: Dec. 23, 1985

§ 102(e) Date: Dec. 23, 1985

[87] PCT Pub. No.: WO85/05183

PCT Pub. Date: Nov. 21, 1985

[30] Foreign Application Priority Data

May 4, 1984 [DE] Fed. Rep. of Germany ....... 3416594

[51] Int. Cl.$^4$ .............................................. G01J 1/00
[52] U.S. Cl. .................................... 250/339; 250/341
[58] Field of Search ..................... 250/339, 341, 358.1, 250/338

[56] References Cited

U.S. PATENT DOCUMENTS 4,148,783  4/1979  Rasberger et al. .................... 546/16
4,345,150  8/1982  Yamura et al. ....................... 250/341
4,492,867  1/1985  Laarhoven et al. ................. 250/341

FOREIGN PATENT DOCUMENTS

0058466  4/1983  Japan .................................. 250/341
8103140  1/1983  Netherlands ......................... 250/341

Primary Examiner—Janice A. Howell
Assistant Examiner—Richard Hanig
Attorney, Agent, or Firm—Bachman & LaPointe

[57] ABSTRACT

The invention relates to a process for measuring the characteristics of test articles made from plastic, particularly polyethylene or polypropylene, to establish whether they are made from non-regenerated, regenerated or optionally a similar plastic which has been regenerated to a certain extent by the infrared spectrometric measurement of the transmission—absorption in the carbonyl group band range of the plastic. According to the invention, the transmission—absorption is measured in the carbonyl group band range at least two different thicknesses of the same plastic and the thickness dependence of these measurements is used as a measurement criterion. The invention is more particularly used on bottle crates or other large injection moulded articles and can be used for classification preferably with sorting according to ageing criteria, also in the case of test articles made from regenerated material, as well as for the selection of old crates suitable for producing regenerated material. The invention also relates to infrared spectrometric means suitable for performing this process.

14 Claims, 8 Drawing Figures

PROCESS FOR DETERMINING OXIDATION-DEPENDENT CHARACTERISTICS OF SIMILAR PLASTIC ARTICLES, AS WELL AS USES OF THE PROCESS AND APPARATUS FOR PERFORMING THE PROCESS ON LARGE INJECTION MOULDED PRODUCTS, PARTICULARLY BOTTLE CRATES

Bottle crates, as well as other large injection moulded products or other plastic test bodies are not only produced from new material, i.e. so-called virgin or first-time moulded, factory-free plastic, but also in part from regenerated or reclaimed material. As opposed to regenerated plastic, plastic in the form of new material is also called non-regenerated plastic. In the Federal Republic of Germany bottle crates are made almost exclusively from polyethylene (PE) and in fact mainly from low pressure or high density polyethylene (LP/HDPE). It has been found that bottle crates made from regenerated material can be virtually as good as those made from new material, if certain conditions, such as with regard to the degree of oxidation are respected. Completely embrittled old crates are not suitable for producing regenerated material. Regenerated material is generally produced from suitable old crates, accompanied by the addition of a certain amount of new material and optionally accompanied by the removal of certain fractions of the plastic mass of the old crate. Thus, bottle crates made from regenerated material differ with regards the extent of their internal oxidation. Further details regarding bottle crates can be gathered from the publication by Dr. Kremkow, "Flaschenkästen aus Neuware und Flaschenkästen aus Regenerate, Verpackungsprüfstelle Vertragslaboratorium des Deutschen Brauerbundes e.v at the Versuchs und Lehranstalt der Brauerei in Berlin, in "Das Erfrischungsgetränk—Mineralwasser-Zeitung", pp. 262 to 267, copy enclosed.

The invention more particularly relates to such bottle transportation crates, but also to other plastic large injection moulded articles, e.g. plastic pallets, as well as other plastic test articles, provided that comparable problems are involved.

It can be gathered from communication T 22/E2 1980 of the "DEUTSCHER BRAUERBUND E.V." of 8.4.1980, particularly p. 2, second complete paragraph that laboratory testing methods have been developed for a completely satisfactory differentiation between usable and unusable regenerated material by the packaging test centre of the "DEUTSCHER BRAUERBUND E.V.". However, it is not at present possible to differentiate between new material and usable regenerated material. The picture was the same at the Conference held on 2.3.1984 by the Gütegemeinschaft Transportund Lagerbehälter im Qualitätsverband Kunststofferzeugnisse e.V, Gütegruppe Glaschenkasten. At this Conference, the manufacturer of means according to EP-Al No. 0,070,610, which deals with the ageing measurement of bottle crates and the sorting out of unsuitable crates had to admit that a distinction could not be made between bottle crates made from new material and those made from regenerated material.

In the aforementioned publication by Kremkow, p. 262, column 3, middle paragraph, details are given on the information, which has long been known to brewing experts that in the case of bottle crates, it is particularly the gripping ledge or strip which is subject to damage and is located on the upper edge of the crate above the lateral openings in the wall and due to the fact that it is only connected by a few vertical webs it can particularly easily break off. Thus, during mechanical measurements and tests on the ageing state of bottle crates, the gripping ledge has been used for testing the ageing state (German Pat. No. 2,922,535). Thus, according to EP-Al No. 0,070,610, the ageing tests are once again based on the gripping ledge, but in this case infrared spectrometric transmission measurement methods are used. The basic hypothesis was that surface phenomena could be ignored for the ageing of bottle crates, because free radicals (esters) would only form in the plastic surface in a relatively rapid process, whereas as the process decisive for the ageing CO groups (carbonyl groups) were formed to an ever increasing amount in the depth of the crate wall over much longer periods of time than on the surface (EP-Al No. 0,070,610, p. 3, lines 11 to 24). This hypothesis is based on the fact that mechanical strength characteristics of the plastic would be mainly dependent on the internal characteristics of the latter, so that this would appear to be completely plausible. Thus, according to EP-Al No. 0,070,610, the gripping ledge of the bottle crate is infrared spectrometrically irradiated and the absorption on the carbonyl group band measured, this being roughly at wave numbers between 1690 and 1740 $cm^{-1}$, with a maximum at approximately 1720 $cm^{-1}$. However, the same carbonyl groups are present from the outset in the depth of the bottle crate wall when the crates are made from regenerated material the concentration thereof varying as a function of the type of regenerated material. Thus, on the basis of its starting points for the ideas, the test method of EP-Al No. 0,070,610 is unable to differentiate between aged bottle crates made from new material and new bottle crates made from regenerated material. In addition, the carrying out of infrared spectrometric transmission testing processes on foils or plates made from plastic was known from the treatise by R. Nitsche and K. Wolf: Kunststoffe, Springerverlag Berlin/Göttingen/Heidelberg, 1961, Vol. 2 (Practical Plastic Testing), pp. 266 to 269, particularly p. 268.

It has also been known since World War II, that the characteristics of polyethylene and other comparable plastics can be established by infrared spectrometric measuring methods (cf footnote on p. 1 of the article entitled "The Infrared Spectrum of Ethyelene Polymers" by L. H. Cross et al in "Discussion Faraday Society", 1950, pp. 235 to 245). In this publication, p. 243 deals with oxidation by heat action and the middle of p. 244 with photooxidation, with the result that the concentration of carbonyl groups, whilst taking account of the thickness of the particular test objects, can be quantitatively measured infrared spectrometrically in the range of the carbonyl group band.

At the latest since the article by Rugg et al entitled "Infrared Spectrophotometric Studies on Polyethylene, II Oxidation" in "Journal of Polymer Science", Vol. XIII, pp. 535 to 547, 1954, particularly the bottom half of p. 541, it is known that both oxidation under heat influence and photooxidation leas to a carbonyl group formation in the plastic and can be infrared spectrometrically measured as transmission absorption in the carbonyl group band range. The corresponding absorptions differ only in a quantitative manner. Particularly in connection with photooxidation, it is stressed that it leads to a brittleness of the test body. The test bodies used were films with a thickness of 0.8 mm. At the least in the early 1970's, this information appeared in text books, cf the treatise "Stabilisierung und Alterung von Plastwerkstoffen", Vol. II, "Alterung der Plastwerkstoffe", by Prof. Thinius, Verlag Chemie GmbH 1971, pp. 116 to 131, particularly pp. 126 and 127. In addition, the standard draft of the German DIN standard 53 383, part 2, March 1979 (objections by 31.7.1979), which deals with the testing of the oxidation resistance of plastics, particularly HDPE, by furnace ageing, describes the measurement of the oxygen quantity chemically bound by HDPE moulding material decisive for the oxidation resistance time by taking transmission—absorption values in the carbonyl group band range at a wave number of 1720 cm$^{-1}$, the basic test body having a thickness of 0.3 mm.

The aforementioned literature references also disclose that the ageing of plastics is firstly dependent on the photooxidation of solar irradiation and only to a secondary extent on the oxidation resulting from heat action. However, the action of photooxidation only has a relatively limited penetration depth. This can be gathered from the article "Polymers under the weather" by Winslow et al in SPE Journal, July 1972, Vol. 28, pp. 19 to 24, particularly the right-hand column of p. 21. According to this, the oxygen rate increases linearly within 200 hours in the case of 0.09 mm thick polyethylene films, but in an increasingly flat manner in the case of thicknesses between 0.13 and 1.4 mm, so that photooxidation is primarily a surface effect. Corresponding results were obtained for polypropylene. Thus, according to the Hüls publication by Dr. Hahnmann et al "18 Jahre Einsatzerfahrungen mit Flaschenkästen aus Polyäthylen" in "Brauwelt", 7/1979, pp. 183 to 188, reprint: 5163 of Hüls. Chemische Werke Hüls Aktiengesellschaft, D-4370 Marl 1, pp. 1 to 7, particularly right-hand column of p. 4, for the measurement of the ageing state of bottle crates, these surface samples are taken from a 0.02 mm surface layer and investigated infrared spectrometrically for carbonyl groups. The preamble of EP-Al No. 0,070,610 is based on such a prior art, but rejects it as being unsuitable for the measurement of the actual ageing state (p. 2, lines 3 to 15 and p. 3, lines 7 to 24).

Whilst overcoming this prejudice, the present invention is based on the following alternative hypothesis.

Regarding plastics as new materials, it is assumed that there is no carbonyl group concentration or only a negligible concentration thereof in the plastic. Regarding plastics made from regenerated materials, it is assumed that there is a certain position-independent carbonyl group concentration over the entire depth of the plastic. In both cases, no matter whether new or regenerated materials are involved, it is assumed that the ageing-specific processes only take place in a surface layer, whose thickness is small compared with the sample thickness and is e.g. manifested in an increasing embrittlement and consequently susceptibility to notching under the photooxidation influences of sunlight. This hypothesis concurs well with the Applicant's own experiences on bottle crates.

In the case of strict validity of this hypothesis, in the case of test objects made from new material infrared spectrometrically measured values of the transmission—absorption in the carbonyl group band range are independent of the thickness of the irradiated test article. The extent of the measured absorption is solely dependent on the surface oxidation and can consequently be used as a criterion for the ageing state of the test article. Thus, unlike in EP-Al No. 0,070,610, the ageing effect is attributed to a surface effect and not to an integral depth effect.

In the case of test articles made from regenerated material, there is also a surface transmission—absorption in the carbonyl group band range in differing thicknesses as a function of the ageing state of the test articles. In addition, due to the carbonyl groups uniformly incorporated into the depth of the regenerated material, according to Beer's Law, the additionally occurring transmission—absorption values increase linearly in proportion to the thickness change.

However, in practice, the conditions according to the aforementioned hypothesis on which the invention is based do not occur in such a clear cut manner as discussed hereinbefore.

However, it would appear to be justified to solve the hitherto unsolved problem in the case of similar plastic articles, particularly of polyethylene or polypropylene, of measuring the characteristics as to whether they are made from non-regenerated or regenerated plastic, how high the degree of oxidation distributed in the depth is in the case of regenerated plastic and/or how high the degree of surface oxidation is, independently of whether the plastic article is made from regenerated or non-regenerated plastic, in that the IR-transmission in the range of the carbonyl group band is measured at at least two different plastic thicknesses. Measurements of those side bands giving comparable test or measurement results are included as equivalents. Some possible side bands are given in the aforementioned previously published literature. Particular interest is attached to those plastics made from low pressure polyethylene or polypropylene regularly used in bottle crates.

On complete evaluation of the measurement according to the invention, all three sought characteristics can be determined. Thus, in the case of plastic articles made from new material or non-regenerated plastic, the IR-transmission is thickness-independent, whereas in the case of plastic articles made from regenerated materials, it is thickness-dependent, i.e. proportional to the thickness change. In the case of plastic articles made from regenerated material, the proportionality factor with which the IR-transmission changes during the thickness change, or the steepness of the IR-transmission curve as a function of the thickness change is a measure of the degree of the oxidation distributed in the depth of the plastic article and consequently a measure of the degree of regeneration of the plastic. No matter whether the plastic article is made from regenerated or non-regenerated plastic, the degree of surface oxidation is obtained from the extrapolation value of the measured IR-transmission at thickness 0 or almost 0. It is obvious that in the case of practical measurements or tests, it is only necessary to determine two, or even one of the aforementioned characteristics.

The measurements of the IR transmission for different thicknesses can in principle be performed successively, but in fact simultaneous measurement is preferred. In general, it is merely necessary to have a single irradiation of each of the varyingly thick points of the plastic article. However, in special cases and particularly when measuring relatively thin points, consideration will be given to multiple irradiation of the same point of the plastic article.

According to a possible further development of the invention, it is possible to irradiate at least two walls of the test article and consequently spread the thickness measuring range, so as to be able to make an even better distinction between surface effects and depth effects.

The transmission—absorption values obtained according to the invention in the range of the carbonyl group band and optionally the PE-band or a comparable band at different thicknesses can thus be used not only for distinguishing between new material and regenerated material or different types of regenerated material, but also for defining an ageing criterion of the test article, independently of whether the latter is made from new or regenerated material. This is brought about by determining the degree of surface oxidation. In the case of an article made from new material and assuming that the hypothesis according to the invention strictly applies, as a result of the thickness independence of the measurement, the same transmission—absorption values are obtained in the carbonyl group band as in the integrated measurement of the carbonyl group band by irradiation with a single test beam. In the case of test articles made from regenerated plastic, it is possible for the first time to provide a quantitative criterion for surface ageing. It is in fact no longer necessary to take direct note of the characteristic determined, no matter whether it is a test article made from new material or regenerated material oxidized to a differing extent. Thus, it is possible to directly further process the particular test values and give the degree of surface ageing without having to take account of whether and to what extent the test article plastic is regenerated. Thus, this makes it possible for the first time to carry out a true ageing measurement of similar plastic articles for all those cases where the appearance of plastic articles made from regenerated material are to be expected. Thus, this is e.g. regularly the case in the Federal Republic of Germany with bottle crates.

Due to the sensitivity of the measurement according to the invention, in some cases there is no need to have precise values regarding the different thickness of the particular test article. Thus, according to the hypothesis of the invention, in the case of new materials the test result is thickness-independent and in the case of regenerated articles, is proportional to the thickness change and this difference, in the case of an unknown or not accurately known magnitude of the different thickness values can be readily detected after only two measurements, if the thickness difference is sufficiently large. In the same way, in the case of only imprecisely known thickness values, the steepness of the IR-transmission can often still be adequately estimated as a function of the thickness change or the extrapolation value of the IR-transmission to thickness zero. Much the same would apply in many practical cases, even if a non-ideal presence of the inventive hypothesis must be assumed. However, greater reliability is obtained in the case of more accurate values of the fundamental thicknesses of the irradiated test article. These thicknesses can be measured in any conventional manner. However, preference is given to measuring the thickness in an infrared spectrometric manner at or close to the point at which the transmission—absorption measurement of the carbonyl group band takes place, or at a different point at which the same or a comparable thickness can be assumed. This thickness measurement can be carried out at the same time as the measurement of the carbonyl group band, or can take place successively before or after the same. For the purpose of the infrared spectrometric transmission—absorption band measurement, it is appropriate to use any band which is completely or largely independent of the presence of carbonyl groups but, according to Beer's Law is proportional to the concentration of typical groups of the particular plastic, as well as proportional to the irradiated thickness (i.e. proportional to the irradiated plastic material). The so-called PE-band with the characteristic wave numbers 1820—1900—2000 $cm^{-1}$ is particularly suitable in the case of polyethylene, whereas the corresponding PP-band is suitable for polypropylene. However, any other comparable side band can also be used.

It is fundamentally possible to carry out the measurements or tests according to the invention, optionally only with a single test beam, on different similar plastic articles at points of different thickness. However, preference is given to measurements carried out for different thicknesses at points of different thickness of the same plastic article.

It is known per se (EP-A1 No. 0,070,610) to measure at different spectral lines or bands. However, this only considers a calibration of the measurement, in that in the vicinity of the carbonyl group band the basic level of the spectral absorption distribution is determined, in order to be able to measure by differentiation the order to be able to measure by differentiation the quantitative excess of the measured carbonyl group band over the spectrum base line. A measurement of carbonyl group bands at more than one point of the bottle crate or the use of its PE-band in the spectrum for thickness measurement purposes has not been considered.

Apart from bottle crates, the test article can in particular be formed by large injection moulded articles made from low pressure polyethylene and other comparable plastics, e.g. also low pressure polypropylene. This can in particular be gathered from p. 11, right-hand column, paragraphs 3 and 4 from the bottom of a 12 page reprint from KUNSTSTOFFBERATER, No. 8, 10, 1968, Frankfurt/Main, entitled "Probleme bei Spritzgussgrossteilen aus Niederdruck-Polyäthylen, demonstriert am Flaschentransportkasten" by Dr Hahmann et al, Chemische Werke Hüls AG. According to this, physical ageing takes place through increasing embrittlement as a result of chemical decomposition, which only takes place on the surface and which is manifested by fine surface cracking and which leads to the finished articles breaking as a result of the extremely notch effect under load. The criterion given for this in the infrared spectrum is a carbonyl group content of more than 0.3%.

The invention also extends to all other plastic test articles in which measurement can take place in a thickness-dependent manner for differentiating between new material and regenerated material or plastic regenerated to a varying degree, as well as for determining the ageing state on the thickness-dependent measurement curve of the carbonyl group band a distinction can also be made between surface effects and integrated depth effects.

Thus, within its general scope, the invention makes it possible to classify and optionally sort test articles on the basis of their material (new and regenerated material). However, particular significance is attached to a classification and possibly sorting on the basis of the ageing state, in the sense of using the inventive process, whilst measuring the ageing state. A possible example for such a contactless classification and optionally sorting is e.g. shown by the article by Harris in "Automation", January 1970, pp. 53 to 57, where it is stated in the final paragraph on p. 57 and in the abstract on p. 53 that spectrometric sorting processes operating in a contactless manner are being increasingly used in the plastics-processing industry for test articles formed from polyethylene pellets arriving on a transfer line (cf also GB-A No. 2,060,166, U.S. Pat. No. 3,448,268 and French Pat. No. 1,501,766). The aforementioned processing using reflection spectrometry can be carried out using measuring chambers for transmission spectrometry as assumed as known by the aforementioned prior art and whereof a possible construction is described in "Revue Générale de l'Electricité", Vol. 88, No. 9, September 1979, Paris, P. Laurenson et al "Photovieillissement et environnement. Nouveau dispositif de photovieillissement accéléré et élaboration d'isolants de couleurs photostables", pp. 685 to 689.

The invention reveals for the first time a way, using the same contactless classification and optionally sorting processes, to differentiate aged plastic crates or other similar plastic articles and optionally to carry out a selection as to whether they are to be used for regenerated material or are to be eliminated completely. Thus, for the first time an easy possibility is provided for employing a simple contactless and consequently also non-destructive testing method for reliably recovering suitable regenerated material, so as to considerably reduce the consumption of new plastic material.

For the first time, this offers possibilities of obtaining a homogeneous starting material for regeneration and to subsequently detect a plastic article made from such a regenerated material. Thus, the present invention permits a quality-reliable recycling with the appropriate process stages of (1) sorting, (2) homogenizing and restabilizing for regenerated material production, (3) new optimized design and (4) production of plastic articles from regenerated material, i.e. from material-adapted plastic, e.g. mixed from regenerated and new material in accordance with specific formulations. The invention simultaneously supplies values for determining the residual life expectation of the plastic articles produced from the regenerated material. This in particular permits the most modern production procedures for plastic articles from regenerated material using CAE-optimization of the moulds and CAD-optimization of the product.

In the preferred use of the bottle crate, as stated, it is possible to e.g. use as one test point a grip edge zone not shaded against solar radiation and which is e.g. 2.8 to 4.0 mm thick and as a second test point an unshaded lower region of the crate wall, which is e.g. between 1.8 and 2.4 mm thick. However, it is also possible to choose other test points on a test article, which are not shaded against solar radiation, or which are comparably shaded and have different thicknesses. The damage or ageing to the surface must then be looked upon as identical or at least comparable. Thus, in the case of bottle crates, it would be possible to consider an upper edge for the corners of the crate as thick points.

The invention is described in greater detail hereinafter relative to an embodiment of the invention and the attached drawings, wherein show.

Figure 1A:
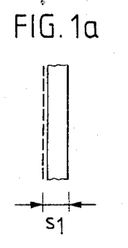
FIGS. 1a and 1b two wall cutouts of different thickness of a test article made from new material.
Figure 1B:
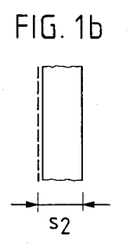
Figure 2A:
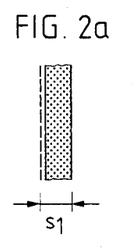
FIGS. 2a and 2b two cutouts corresponding to FIGS. 1a and 1b of a test article made from regenerated material.
Figure 2B:
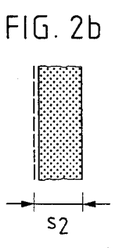
Figure 3:
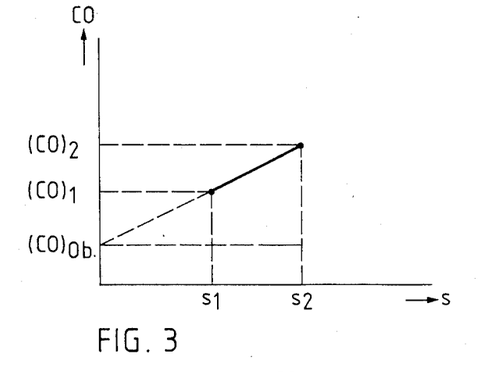
FIG. 3 a graph for representing the dependence of measured transmission—absorption values in the carbonyl group band range as a function of the test article thickness.

The hypothesis on which the invention is based will be firstly explained relative to FIGS. 1 to 3.

$s$ is the thickness or wall thickness of the test article to be irradiated during the infrared spectrometric measurement and $s_1$ and $s_2$ are the thicknesses at two varyingly thick test points of a test article. $s_2$ is significantly larger than $s_1$. The test article of FIGS. 1a and 2a can have a wall thickness $s_1$, whilst the article of FIGS. 1b and 2b has a thickness $s_2$. In the case of FIGS. 1a and 1b, these are preferably, but not necessarily, varyingly thick points of the same test article and this also applies to FIGS. 2a and 2b.

The test points shown in FIGS. 1a and 1b correspond to test articles made from new material, whereas those shown in FIGS. 2a and 2b correspond to articles made from regenerated material. In the regenerated material, carbonyl or CO-groups are distributed with a uniform concentration in the depth and this is indicated by corresponding dotting in FIGS. 2a and 2b, which is omitted in FIGS. 1a and 1b, because freedom from carbonyl groups in the depth is assumed in the case of new material.

A dotted line is also visible on the left-hand side of FIGS. 1a/1b and 2a/2b, which symbolizes a surface zone of the test article, whose depth is negligible compared with the thickness or wall thickness $s_1$ or $s_2$ of the particular test article.

Without restricting the general nature, it is assumed for illustrating purposes that such a surface zone is only present on one side of the test article. However, in principle such a surface zone can be present on both sides of the test article, although generally one surface side is exposed to photooxidation by solar irradiation to a greater extent than the other side.

The proportion of the measured transmission—absorption in the carbonyl group band and which emanates from the surface zone is $(CO)_{ob}$. In the case of mould-fresh test articles, this value is equal to or close to zero. No matter whether a new or regenerated material article is involved, it can rise to a particular threshold value which, in the case of differentiation, can also depend on the nature of the material (whether it is a new or regenerated material, or also the oxygen-containing nature of the regenerated material). Above said threshold value a surface brittleness must be assumed which would lead to the particular test article being discarded as sensitive to destruction.

The (calibrated) transmission—absorption measured over the specific thicknesses $s_1$ and $s_2$ is designated $(CO)_1$ or $(CO)_2$ or, as a general variable, as CO in the carbonyl group band range. This leads to the representation of FIG. 3, bearing in mind the fact that according to Beer's Law, the increase of the carbonyl groups with the thickness is proportional to their concentration and to the thickness.

According to the optical path, this can be expressed by the following equation:

$$\frac{(CO)_2 - (CO)_{ob}}{(CO)_1 - (CO)_{ob}} = \frac{s_2}{s_1} \quad (1)$$

resolved according to $(CO)_{ob}$ it follows:

$$(CO)_{ob} = \frac{s_2(CO)_1 - s_1(CO)_2}{s_2 - s_1} \quad (2)$$

Figure 3A:
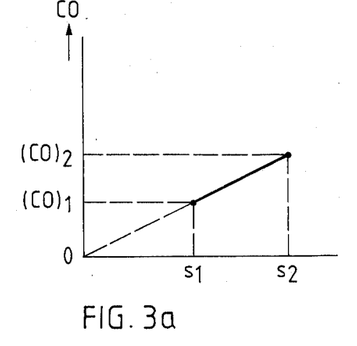
FIGS. 3a and 3b variants of the graph of FIG. 3.
Figure 3B:
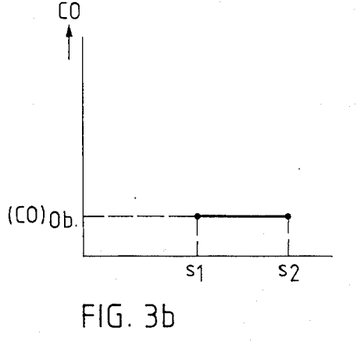

FIGS. 1a and 1b relate to a new material test article, then the following special case according to FIG. 3b applies:

$$(CO)_{ob} = (CO)_1 = (CO)_2 \quad (3)$$

In the case of unaged test articles made from new material with $(CO)_{ob} = 0$ in FIG. 3b, the test values at $s_1$ and $s_2$ are also on the abscissa. Otherwise, from threshold value $(CO)_{ob}$, CO increases linearly with the thickness s. In this case, it is a regenerated material test article according to FIGS. 2a and 2b, the same carbonyl group concentration being assumed at the points of different thickness.

FIG. 3a corresponds to the test result on a test body made from not yet aged regenerated material with $(CO)_{ob} = 0$. In all cases, the extrapolated value of $(CO)_{ob}$ can be looked upon as a critical value of the ageing. Thus, the concentration of these carbonyl groups, i.e. a characteristic parameter for the nature of the regenerated material, can be determined from the steepness, i.e. the differential quotient, of the test curve according to FIG. 3 or 3a.

The invention is also based on the assumption that this applies if in practice the conditions of this hypothesis do not exist in a pure form. Even them, conclusions can be drawn from the form of the absorption dependence on the thickness in the sense of FIG. 3 between new and regenerated materials, regarding the degree of oxidation of the regenerate from the differential quotient and the surface oxidation as a critical parameter for the ageing of the test article from the extrapolated value $(CO)_{ob}$ and in the latter case no matter whether it is a test article made from new material or regenerated material with a greater or lesser carbonyl group content.

The aforementioned parameters can therefore be used in the known manner for the classification and optionally sorting according to new material or regenerated material, the nature of the regenerated material, the ageing state and the suitability of an old crate for obtaining regenerated material.

Figure 4:
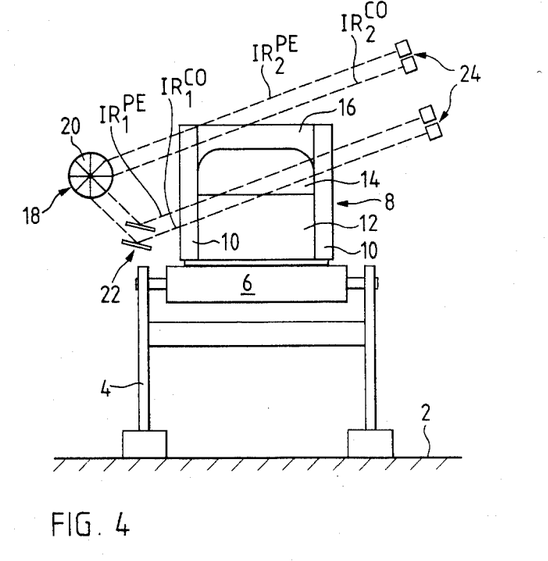
FIG. 4 a side view of an apparatus for performing the process according to the invention.

FIG. 4 will now be used for illustrating a preferred apparatus for performing the process according to the invention. On a base 2 is placed a bearing support 4 of a roller train 6 enabling bottle crates 8 to be successively passed into the represented measuring or test apparatus. The roller train 6 is only one example from numerous possible transfer lines. It is also possible e.g. to use belt conveyors, circular conveyors, etc. The bottle crates 8 are also only a preferred example of the many different possible test articles, particularly large injection moulded articles.

The bottle crate 8 is shown with reinforced corner pillars 10, between which extends side walls made from a relatively thin, film-like, lower side wall portion 12, a gripping opening 14 above it and a gripping ledge or strip 16. The wall thickness of the corner pillar 10 and the gripping ledge 18 is larger roughly by a factor of 2 or more than the wall thickness, of the lower side wall portion 12, whose thickness is typically approximately 1.5 cm. The bottle crate 8 can be made from low pressure or high density polyethylene.

An infrared light source 18 is equipped with two filters, whereof one only lets through infrared light with wave numbers corresponding to the carbonyl group band, whilst the other lets through infrared light corresponding to the PE-band. The corresponding filtering means is symbolically designated by 20.

The two infrared light beams of different wavelengths are in each case split into at least two partial beams, which are passed through points of different thickness of bottle crate 8. Such a beam splitting can e.g. be brought about by a semireflecting mirror.

In the represented embodiment, one partial beam from the infrared light source passes in a linear manner into bottle crate 8, whilst the other partial beam is deflected by a mirror means 22 to the other test point on crate 8. However, the partial beams can be deflected in some other way by known optical means. However, the present arrangement, in which all the partial beams are parallel to one another has apparatus advantages. Thus, as shown, the infrared light source 18, together with the filters 20 and the mirror means 22 could be placed adjacent to one side of crate 8 and four receivers 24 for each partial beam adjacent to the other side of crate 8 and here appropriately somewhat higher, so that despite the presence of four test points it is easy to obtain access to the apparatus from above. The infrared beams IR have the superscript CO when their wave numbers correspond to the carbonyl group band and the superscript PE when they correspond to the polyethylene band.

In accordance with the discussion relative to FIGS. 1 to 3, subscripts 1 or 2 are used for designating test beams, which are passed through the thinner test point 1 or the thicker test point 2. In this case, the thinner test point 1 is the lower side wall portion 12 which normally carries advertisements, whereas the thicker test point is either the gripping ledge 16 (in a lower area not shaded by an all-round edge) or an unshaded, upper end region of a corner pillar 10, or a not shown, e.g. flange-like upper bottom rim. The representation of FIG. 2 is suitable for all three possibilities. The actual irradiation points at test points 1 and 2 are not identical, but are so close together that it is possible to assume the same wall thicknesses. However, irradiation at substantially the same test points is possible, provided that it is possible to separately process the test beams on the carbonyl group band on the one hand and the PE band on the other.

In the present embodiment, the test beams reach the test point 1 through a lower side wall portion 2 and then leave the bottle crate through the opposite grip opening 14, so that there is only a single irradiation of the wall. The test beams at test point 2, following irradiation of the first wall, pass directly upwards over the bottle crate 8, so that they do not reach the opposite crate wall. As a result of this irradiation of only a single crate wall, the test beams slope from bottom to top. However, it is appropriately possible to modify the optical path in such a way that in each case two facing walls are simultaneously irradiated by the same test beam IR. This can e.g. lead to a horizontal, parallel optical path. However, the parallelism of the beams is not a functional requirement and is merely appropriate in some cases for apparatus simplicity purposes.

It can be sufficient in certain uses to only provide test beams $IR^{CO}$ and to cut out or not provide from the outset the test beams $IR^{PE}$. This is particularly the case if a distinction is only to be made between bottle crates of new material and regenerated material. In the case of ageing measurements and usually also measurements for the internal degree of oxidation of regenerated material, it is better to increase the precision of the measurements by additional use of beams $IR^{PE}$. Thus, a particularly preferred apparatus provides all four test beams, or also further test beam pairs and certain of these can be put out of operation as required.

When using all four test beams IR, the transmission—absorption values obtained on the four receivers 24 are passed via a multiplexer (interrogator) to an analog converter, which passes the values to a connected computer for evaluation and decision, as to whether the investigated bottle crate 8 can be passed as usable, whether through reaching a certain CO-group concentration on the surface it is to be separated for regeneration purposes or whether on exceeding a maximum CO-group concentration on the surface and in particular in the case of regenerated material crates, it is to be discarded as unusable, i.e. it will not be regenerated again.

A multiple passage through the walls of the test article, in this case the bottle crate 8, can also be brought about in that by providing corresponding mirror means (including other optical deflection elements), the same wall can be traversed on a number of occasions by one test beam. For example, the transmitter and receiver could be located on the same side of the crate, whilst arranging a mirror means either above the crate, behind the gripping openings or, which would lead to increased constructional expenditure, within the crate and using timed introduction.

In general, a single wall irradiation is sufficient, particularly as it has minimum reflection losses. It is appropriate to guide all the test beams in such a way that there is no contact with the crate compartmentalization.

We claim:

1. A method for determining oxidation characteristics of similar plastic articles made from at least one of polyethylene and propylene and to classify from said characteristics at least one of whether said articles are made from plastic which has been regenerated or a non-regenerated plastic, how high a degree of depth-distribution is present in the case of said articles being formed from said regenerated plastic, and how high a degree of surface oxidation is present independent of whether said plastic articles are formed from said regenerated or non-regenerated plastic, said method comprising measuring an IR-transmission absorption in the carbonyl group band range as an indication of said oxidation characteristics at at least two different plastic thicknesses of the same plastic material, and determining from said measurements a part of said measured transmission-absorption within the carbonyl groups band range which emanates from a surface zone, said determination being made in accordance with the following equation:

$$(CO)_{ob} = \frac{S_2(CO)_1 - S_1(CO)_2}{S_2 - S_1}$$

wherein $(CO)_{ob}$ = the part of the measured transmission-absorption in the carbonyl group band range which emanates from the surface zone;
$S_1$ = a thickness at a first point;
$S_2$ = a thickness at a second point;
$(CO)_1$ = the transmission-absorption measured over the thickness at the first point; and
$(CO)_2$ = the transmission-absorption measured over the thickness at the second point such that said $(CO)_{ob}$ value is used to classify said oxidation characteristics of said plastic articles.

2. A method according to claim 1 wherein said measuring step comprises passing at least two test beams with wave numbers in the carbonyl group band range of the plastic material at least once through varyingly thick points of said plastic material.

3. A method according to claim 2 further comprising determining said thicknesses by measuring an IR-transmission in the range of a band dependent on the irradiated plastic concentration but independent of the carbonyl groups in accordance with Beer's Law.

4. A method according to claim 3 wherein said second measuring step comprises passing at least two test beams with wave numbers of a band dependent on the irradiated plastic concentration of the plastic article but independent of the carbonyl groups through a plurality of points corresponding to at least one of the same points at which the IR-transmission in the carbonyl group band range are passed through said plastic material and points corresponding to different thicknesses of said plastic material.

5. A method according to claim 4 wherein said measurements performed at different thicknesses are carried out at points of different thickness of the same plastic article.

6. A method according to claim 4 wherein each said measuring step comprises simultaneously irradiating several walls of one of said plastic articles.

7. A method according to claim 4 wherein said articles comprise large injection moulded articles such as bottle transportation crates.

8. A method according to claim 5 wherein said measuring steps each comprise passing at least one of said test beams through an area of at least one of a gripping ledge, a corner pillar, and an upper edge which is normally freely exposed to sunlight and another of said test beams through a portion of a lower side wall of a bottle crate which is normally freely exposed to sunlight.

9. A method according to claim 1 wherein plastic articles which are no longer usable are eliminated.

10. A method according to claim 1 wherein plastic articles suitable as regenerated material are sorted out.

11. An apparatus for determining oxidation characteristics of similar plastic articles made from at least one of polyethylene and polypropylene and to classify from said oxidation characteristics at least one of whether said articles are made from a regenerated or non-regenerated plastic, how high a degree of depth distribution is present in the case of said articles being formed from said regenerated plastic, and how high a degree of surface oxidation is present independent of whether said plastic articles are formed from said regenerated or non-regenerated plastic, said apparatus comprising: means for measuring at least an IR transmission-absorption in the carbonyl group band range as an indication of said oxidation characteristics at at least two different thicknesses of the same plastic material, said measuring means comprising a transmitter capable of transmitting a plurality of IR beams having different desired wavelengths including one having a wavelength in the carbonyl group band range, an optical device for splitting radiation at a desired wavelength from said transmitter into at least two test beams so that said test beams pass through varyingly thick areas of said plastic material, and means for receiving said test beams; and means for determining from said received test beams a part of said measured transmission absorption within the carbonyl group band range which emanates from a surface zone in accordance with the following equation:

$$(CO)_{ob} = \frac{S_2(CO)_1 - S_1(CO)_2}{S_2 - S_1}$$

wherein $(CO)_{ob}$ = the part of the measured transmission-absorption in the carbonyl group band range which emanates from the surface zone.

$S_1$ = a thickness at a first point $S_2$ = a thickness at a second point $(CO)_1$ = the transmission-absorption measured over the thickness at the first point; and $(CO)_2$ = the transmission-absorption measured over the thickness at the second point such that said $(CO)_{ob}$ value is used to classify said oxidation characteristics of said plastic articles.

12. An apparatus according to claim 11 wherein said plastic material is accessible from above.

13. An apparatus according to claim 11 wherein said test beams run parallel to one another.

14. An apparatus according to claim 11 wherein said test beams slope from the bottom to the top of said plastic material.

* * * * *

UNITED STATES PATENT AND TRADEMARK OFFICE
CERTIFICATE OF CORRECTION

PATENT NO. : 4,719,351

DATED : January 12, 1988

INVENTOR(S) : CHRISTOPH SCHOELLER ET AL.

It is certified that error appears in the above-identified patent and that said Letters Patent is hereby corrected as shown below:

Column 11, claim 1, line 3, after "said", and before "characteristics", the word --oxidation-- was omitted Signed and Sealed this Thirtieth Day of August, 1988

*Attest:*

DONALD J. QUIGG

*Attesting Officer*   *Commissioner of Patents and Trademarks*